US010300236B2

(12) United States Patent
Cortez, Jr. et al.

(10) Patent No.: US 10,300,236 B2
(45) Date of Patent: May 28, 2019

(54) QUIET NASAL CANNULA

(71) Applicant: Vapotherm, Inc., Stevensville, MD (US)

(72) Inventors: Felino V. Cortez, Jr., Bowie, MD (US); William F. Niland, Arnold, MD (US); George McGarrity, Centreville, MD (US)

(73) Assignee: VAPOTHERM, INC., Exeter, NH (US)

( * ) Notice: Subject to any disclaimer, the term of this patent is extended or adjusted under 35 U.S.C. 154(b) by 887 days.

(21) Appl. No.: 13/665,100

(22) Filed: Oct. 31, 2012

(65) Prior Publication Data

US 2014/0116447 A1     May 1, 2014

(51) Int. Cl.
*A61M 16/06*     (2006.01)
*A61M 16/08*     (2006.01)
(Continued)

(52) U.S. Cl.
CPC ..... *A61M 16/0666* (2013.01); *A61M 16/0672* (2014.02); *A61M 16/0875* (2013.01); *A61M 16/1075* (2013.01); *A61M 16/16* (2013.01)

(58) Field of Classification Search
CPC .. A61M 16/00; A61M 16/06; A61M 16/0605; A61M 16/0666; A61M 16/0672;
(Continued)

(56) References Cited

U.S. PATENT DOCUMENTS 2,735,432 A    2/1956 Hudson
2,868,199 A    1/1959 Hudson
(Continued)

FOREIGN PATENT DOCUMENTS

CN    101098726    1/2009
EP    1342484      9/2003
(Continued)

OTHER PUBLICATIONS

International Search Report dated Jan. 30, 2014, application No. PCT/US2013/067407.
(Continued)

*Primary Examiner* — Michael J Tsai
(74) *Attorney, Agent, or Firm* — White & Case LLP

(57) ABSTRACT

Devices for providing respiratory therapy to a patient are disclosed. One device includes first and second elongated lumens and a nosepiece. The elongated lumens each have a constant internal diameter. The nosepiece portion has a third lumen and a fourth lumen. The third and fourth lumens have constant internal diameters equal to those of the first and second lumens. The third and fourth lumens have inlet ends adapted to be connected to the outlet ends of the first and second lumens without constricting the internal diameter of the first and second lumens. The third and fourth lumens are configured to receive first and second flows of breathing gas from the first and second lumens and deliver the flows of breathing gas to outlets end of the third and fourth lumens. The second flow of breathing gas is maintained separate from the first flow of breathing gas within the nosepiece portion.

16 Claims, 3 Drawing Sheets

(51) Int. Cl.
*A61M 16/10* (2006.01)
*A61M 16/16* (2006.01)

(58) Field of Classification Search
CPC ...... A61M 16/0677; A61M 2016/0661; A61M 2039/1061; A61M 39/00; A61M 2205/42
See application file for complete search history.

(56) References Cited

U.S. PATENT DOCUMENTS

| | | | |
|---|---|---|---|
| 3,513,844 A | | 5/1970 | Smith |
| 3,643,660 A | * | 2/1972 | Hudson et al. .......... 128/207.18 |
| 3,726,275 A | | 4/1973 | Jackson |
| 3,802,431 A | | 4/1974 | Farr |
| 4,106,505 A | | 8/1978 | Salter |
| 4,273,124 A | | 6/1981 | Zimmerman |
| 4,278,082 A | * | 7/1981 | Blackmer ................ 128/207.18 |
| 4,422,456 A | | 12/1983 | Tiep |
| 4,535,767 A | | 8/1985 | Tiep |
| 4,648,398 A | | 3/1987 | Agdanowski |
| 4,660,555 A | | 4/1987 | Payton |
| 4,736,741 A | | 4/1988 | Payton et al. |
| 4,742,824 A | | 5/1988 | Payton et al. |
| 4,753,233 A | | 6/1988 | Grimes |
| 4,808,160 A | | 2/1989 | Timmons |
| 4,995,384 A | | 2/1991 | Keeling |
| 5,025,805 A | | 6/1991 | Nutter |
| 5,046,491 A | | 9/1991 | Derrick |
| 5,404,885 A | | 4/1995 | Sheehan et al. |
| 5,509,409 A | | 4/1996 | Weatherholt |
| 5,526,806 A | | 6/1996 | Sansoni |
| 6,655,385 B1 | | 12/2003 | Curti |
| 6,679,265 B2 | | 1/2004 | Strickland |
| 6,763,832 B1 | | 7/2004 | Kirsch |
| 6,776,163 B2 | | 8/2004 | Dougill |
| 6,799,575 B1 | | 10/2004 | Carter |
| 6,913,017 B2 | | 7/2005 | Roberts |
| 7,146,979 B2 | | 12/2006 | Seakins |
| 7,493,902 B2 | * | 2/2009 | White et al. ............. 128/207.18 |
| 7,775,210 B2 | * | 8/2010 | Schobel (nee Bauer) et al. ......... 128/207.18 |
| 2002/0157673 A1 | | 10/2002 | Kessler |
| 2003/0209246 A1 | | 11/2003 | Schroeder et al. |
| 2004/0035430 A1 | | 2/2004 | Wright |
| 2005/0029757 A1 | | 2/2005 | Fiebing |
| 2005/0039757 A1 | | 2/2005 | Wood |
| 2005/0121038 A1 | | 6/2005 | Christopher |
| 2005/0161049 A1 | | 7/2005 | Wright |
| 2006/0005842 A1 | | 1/2006 | Rashad |
| 2006/0130840 A1 | | 6/2006 | Porat et al. |
| 2006/0180151 A1 | * | 8/2006 | Rinaldi ............ A61M 16/0666 128/206.11 |
| 2008/0051674 A1 | * | 2/2008 | Davenport et al. .......... 600/561 |
| 2008/0190436 A1 | | 8/2008 | Jaffe et al. |
| 2011/0067704 A1 | | 3/2011 | Kooij et al. |
| 2011/0125052 A1 | | 5/2011 | Davenport et al. |
| 2013/0042862 A1 | * | 2/2013 | Buch et al. ............. 128/202.16 |

FOREIGN PATENT DOCUMENTS

| | | |
|---|---|---|
| EP | 1695732 | 8/2006 |
| WO | WO-0064521 A1 | 11/2000 |
| WO | WO-2005/014080 | 2/2005 |
| WO | WO-2005011556 A2 | 2/2005 |
| WO | WO-2005011556 A2 | 2/2005 |
| WO | WO 2006072231 A2 | 7/2006 |
| WO | WO-2007111935 A2 | 10/2007 |
| WO | WO-2008/019294 | 2/2008 |
| WO | WO 2010/102094 A1 | 9/2010 |

OTHER PUBLICATIONS

International Application Serial No. PCT/US2007/023973, International Search Report dated Aug. 12, 2008, 5 pgs.
International Application Serial No. PCT/US2007/023973, International Written Opinion dated Aug. 12, 2008, 11 pgs.
International Search Report for PCT/US2013/067407 dated May 5, 2015.
European Supplementary Search Report for Application No. 13851754.5 dated Mar. 21, 2016.

\* cited by examiner

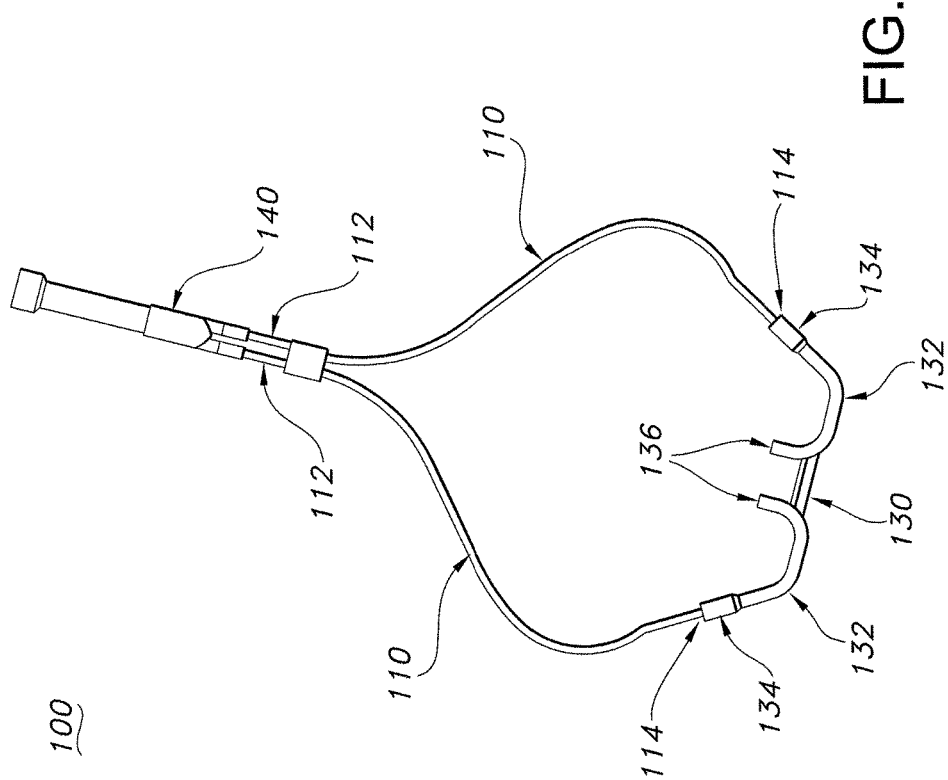

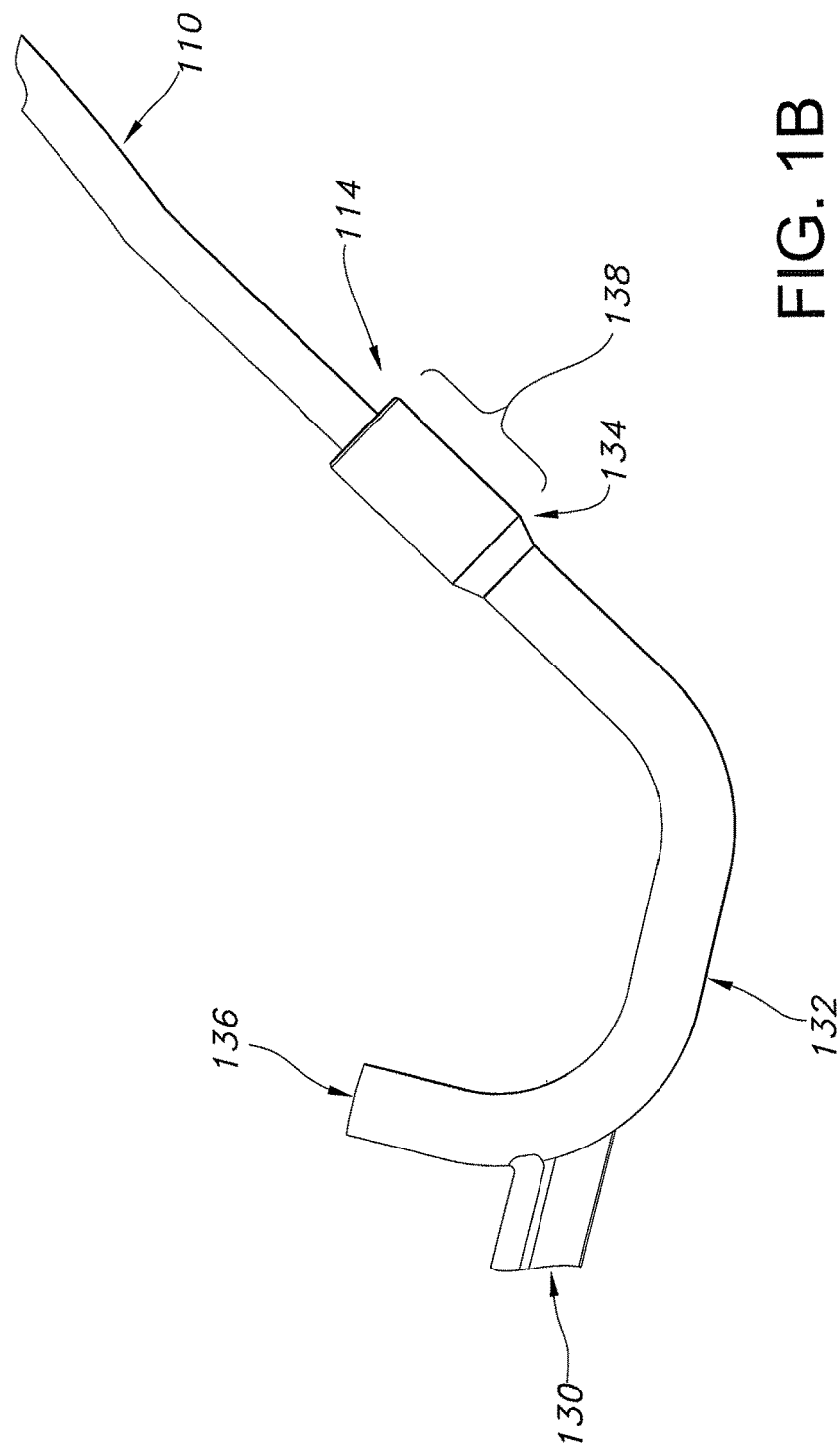

QUIET NASAL CANNULA

FIELD OF THE INVENTION

The present invention relates generally to respiratory therapy, and more particularly to devices for use in providing respiratory therapy.

BACKGROUND OF THE INVENTION

Patients with respiratory ailments may be administered a supplemental flow of breathing gases, such as oxygen, for example, to aid in respiration. These breathing gases are typically provided from a breathing gas supply, such as an oxygen tank, to a patient interface. The patient interface may be coupled to the breathing gas supply and in communication with a patient's nasal passages for delivery of the flow of breathing gas to the patient for nasal or oral inhalation. The flow of breathing gas provided to the patient may be selected based on the patient's inspiratory rate and the patient's respiratory ailment.

One common patient interface is a nasal cannula. A nasal cannula typically includes one or more nasal prongs, with each prong inserted into a respective nostril during use. The nasal cannula may optionally be retained during use by looping tubing attached to the cannula over the user's ears and drawing the tubing tight under the user's chin, or may be secured to the user by some other means. A conventional nasal cannula is described in U.S. Patent Application Publication No. U.S. 2008/0121230 A1.

Improved devices for respiratory therapy are desired.

SUMMARY OF THE INVENTION

Aspects of the present invention are directed to devices for providing respiratory therapy to a patient. In accordance with one aspect of the present invention, a device for providing respiratory therapy to a patient comprises a pair of elongated lumens and a nosepiece. The first elongated lumen has a constant internal diameter. The first lumen has an inlet end and an outlet end. The second elongated lumen has a constant internal diameter. The second lumen has an inlet end and an outlet end. The nosepiece portion is configured to be connected to the outlet ends of the first and second lumens. The nosepiece portion has a third lumen and a fourth lumen. The third lumen has a constant internal diameter equal to the constant internal diameter of the first lumen. The third lumen has an inlet end adapted to be connected to the outlet end of the first lumen without constricting the internal diameter of the first lumen. The third lumen is configured to receive a first flow of breathing gas from the first lumen and deliver the first flow of breathing gas to an outlet end of the third lumen. The fourth lumen has a constant internal diameter equal to the constant internal diameter of the second lumen. The fourth lumen has an inlet end adapted to be connected to the outlet end of the second lumen without constricting the internal diameter of the second lumen. The fourth lumen is configured to receive a second flow of breathing gas from the second lumen and deliver the second flow of breathing gas to an outlet end of the fourth lumen. The second flow of breathing gas is maintained separate from the first flow of breathing gas within the nosepiece portion.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. According to common practice, the various features of the drawings are not drawn to scale, unless otherwise indicated. To the contrary, the dimensions of the various features may be expanded or reduced for clarity. Included in the drawings are the following figures:

FIG. 1A is an image illustrating an exemplary device for providing respiratory therapy to a patient in accordance with aspects of the present invention;

FIG. 1B is an enlarged image illustrating a nosepiece portion of the exemplary device of FIG. 1A.

DETAILED DESCRIPTION OF THE INVENTION

Figure 1C:
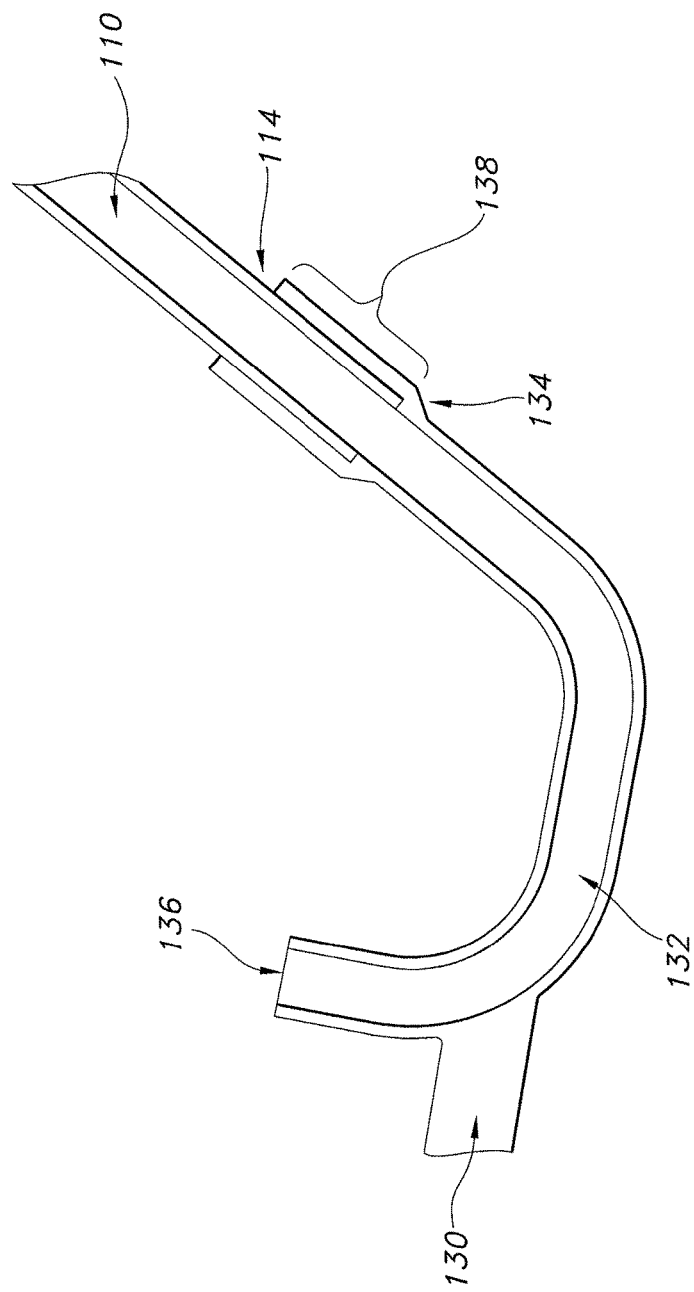
FIG. 1C is a cross-sectional view of the nosepiece portion of FIG. 1B.

Embodiments of the present invention are directed to devices for providing respiratory therapy to a patient. These exemplary embodiments are particularly suitable to provide high flows of breathing gas to a patient while minimizing noise created during breathing gas delivery. The disclosed embodiments may thereby achieve quieter breathing gas delivery than convention nasal cannulas.

As a general overview, the disclosed embodiments of the present invention minimize noise creation during breathing gas delivery by preventing disruptions (e.g. eddies) in breathing gas flow. The disclosed embodiments also prevent other disruptions in the flow of breathing gas, including decreasing loss of heat from the breathing gas, decreasing liquid formation/liquid spray to patient, and decreasing excess water dripping. These disruptions in breathing gas flow may be prevented with a number of different features encompassed by the present invention, including, for example, (i) providing a channel for breathing gas flow that maintains a substantially constant internal diameter; (ii) preventing separate breathing gas flows from mixing with each other; and/or (iii) preventing sharp changes in direction of breathing gas flow.

Referring now to the drawings, FIGS. 1A-1C illustrate an exemplary device 100 for providing respiratory therapy to a patient in accordance with aspects of the present invention. Generally, device 100 includes a pair of elongated lumens 110 and a nosepiece portion 130. Additional details of device 100 will be described herein.

Lumens 110 provide flow paths for providing breathing gas to the patient. As shown in FIG. 1A, each lumen 110 has an inlet end 112 for receiving the flow of breathing gas and an outlet end 114 for transmitting the flow of breathing gas. In an exemplary embodiment, lumens 110 are elongated flexible tubes. Suitable tubes for use as lumens 110 will be known to one of ordinary skill in the art from the description herein.

Each illustrated lumen 110 has a constant internal diameter, i.e., an internal diameter that is substantially constant along the entire length of the lumen 110. The constant internal diameter of one lumen 110 may be approximately equal to or different from the constant internal diameter of the other lumen 110. In an exemplary embodiment, each lumen 110 has a constant internal diameter dependent on its intend use: for infants, approximately 0.055 inches; for pediatric patients, approximately 0.075 inches; for adults, approximately 0.125 inches. Lumens 110 may also have the approximately equal lengths, or may have different lengths. In an exemplary embodiment, lumens 110 each have a length of between approximately 10-18 inches.

While lumens 110 may in an exemplary embodiment comprise flexible tubing, it may be desirable that the flexibility of lumens 110 be limited, e.g., in order to prevent sharp changes in direction of the flow of breathing gas within lumens 110. The flexibility of lumens 110 may be limited, for example, based on the materials and thicknesses selected for the walls of lumen 110, as would be understood by one of ordinary skill in the art from the description herein. In an exemplary embodiment, lumens 110 have a minimum radius of curvature of approximately one half inch along their respective lengths.

Nosepiece portion 130 receives the breathing gas from lumens 110. Nosepiece portion 130 is configured to be connected to the outlet ends 114 of lumens 110. As shown in FIGS. 1A and 1B, nosepiece portion 130 includes a pair of lumens 132. Each lumen 132 has an inlet end 134 for receiving the flow of breathing gas from lumen 110, and an outlet end 136 for delivering the flow of breathing gas to the patient. As will be described in greater detail below, inlet end 134 of lumen 132 is adapted to be connected to outlet end 114 of lumen 110. Outlet end 136 of lumen 132 is adapted to be positioned within the nare of the patient, for inhalation of the breathing gas by the patient. Thus, outlet ends 136 function as nasal prongs of nosepiece portion 130. As shown in FIG. 1A, each lumen 132 maintains its respective flow of breathing gas separate from the flow of breathing gas in the other lumen 132.

Each illustrated lumen 132 has a constant internal diameter. The constant internal diameter of one lumen 132 may be approximately equal to or different from the constant internal diameter of the other lumen 132. However, the constant internal diameter of each lumen 132 is equal to the constant internal diameter of the respective lumen 110 to which it is coupled.

As set forth above, each lumen 132 is adapted to be connected with a respective lumen 110. When connected, each pair of lumens 110 and 132 defines a substantially constant diameter flow path for a flow of breathing gas, extending from the inlet 112 of lumen 110 to the outlet 136 of lumen 132. In order to maintain a substantially constant diameter flow path, lumen 132 is connected to lumen 110 without constricting the internal diameter of lumen 110. The invention is not limited to any particular mechanism for connecting lumen 110 with lumen 132. An exemplary embodiment is provided herein for the purposes of illustration.

FIG. 1B illustrates an exemplary mechanism for coupling outlet end 114 of lumen 110 to inlet end 134 of lumen 132. As shown in FIG. 1B, inlet end 134 of lumen 132 comprises an enlarged portion 138. Enlarged portion 138 has a larger internal diameter than the rest of lumen 132. Specifically, enlarged portion 138 has an internal diameter substantially equal to an external diameter of outlet end 114 of lumen 110. Accordingly, outlet end 114 of lumen 110 can be slidably positioned within enlarged portion 138 in a friction fitting. In this position, the constant internal diameter of lumen 110 transitions with minimal interruption into the equal constant internal diameter of lumen 132, thereby maintaining a substantially constant diameter flow path for the flow of breathing gas, as shown in FIG. 1C. While FIGS. 1B and 1C illustrate nosepiece portion 130 as including the enlarged portion, it will be understood that it is not so limited. The enlarged portion may be located on either nosepiece portion 130 or on lumen 110.

In an exemplary embodiment, nosepiece portion 130 is formed from a flexible material, e.g., silicone rubber. Accordingly, lumens 132 may desirably be shaped to prevent sharp changes in direction of the flow of breathing gas within lumens 132, as described above with respect to lumens 110. In an exemplary embodiment, lumens 132 have a minimum radius of curvature of approximately one quarter inch along their respective lengths.

Device 100 is not limited to the above components, but may include alternative or additional components, as would be understood by one of ordinary skill in the art from the description herein.

Device 100 may further include a connector 140. Connector 140 is adapted to be connected to inlet ends 112 of lumens 110. Connector 140 defines an inlet port 142 and is configured to be connected to a delivery tube from a source of breathing gas. Connector 140 is desirably connected to lumens 110 without constricting the constant internal diameters of lumens 110, as described above with respect to nosepiece portion 130. Accordingly, connector 140 may include similar coupling mechanism(s) to those used by nosepiece portion 130.

Device 100 may further include a source of breathing gas for inhalation by the patient. In an exemplary embodiment, the source generates heated and humidified breathing gas for delivery to the patient. The source may be configured to provide breathing gas at flow rates between 1 and 8 liters per minute (lpm) for infants, between 5 and 20 lpm for pediatric patients, or up to 40 lpm for adults. Suitable sources of heated and humidified gas will be known to one of ordinary skill in the art. For example, the source may be the Vapotherm Flowrest System, Vapotherm Careflow System, Precision Flow unit, or the Vapotherm 2000i, all of which are provided by Vapotherm, Inc. of Stevensville, Md., USA. Other suitable sources of breathing gas will be known to one of ordinary skill in the art from the description herein.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A device for providing respiratory therapy to a patient comprising:
   a first elongated lumen having a constant internal diameter, the first lumen having an inlet end and an outlet end;
   a second elongated lumen having a constant internal diameter, the second lumen having an inlet end and an outlet end; and
   a nosepiece portion configured to be connected to the outlet ends of the first and second lumens, the nosepiece portion having:
   a third lumen having a constant internal diameter equal to the constant internal diameter of the first lumen, the third lumen having an inlet end adapted to be connected to the outlet end of the first lumen without constricting the internal diameter of the first lumen, the third lumen configured to receive a first flow of breathing gas from the first lumen and deliver the first flow of breathing gas to an outlet end of the third lumen;
   a fourth lumen having a constant internal diameter equal to the constant internal diameter of the second lumen, the fourth lumen having an inlet end adapted to be connected to the outlet end of the second lumen without constricting the internal diameter of the second lumen, the fourth lumen configured to receive a second flow of breathing gas from the second lumen and deliver the second flow of breathing gas to an outlet end of the fourth lumen, the second flow of breathing gas maintained separate from the first flow of breathing gas within the nosepiece portion; and a source of heated and humidified breathing gas connected to the inlet ends of the first and second lumens, the source being configured to provide breathing gas at flow rates of about 40 liters per minute;

wherein the first lumen and the nosepiece portion define a constant diameter flow path for the first flow of breathing gas from the inlet end of the first lumen to the outlet end of the third lumen; and wherein the second lumen and the nosepiece portion define a constant diameter flow path for the second flow of breathing gas from the inlet end of the second lumen to the outlet end of the fourth lumen.

2. The device of claim 1, wherein
one of the inlet end of the third lumen and the outlet end of the first lumen comprises an enlarged portion, the enlarged portion having an internal diameter substantially equal to an external diameter of the other one of the inlet end of the third lumen and the outlet end of the first lumen, and
one of the inlet end of the fourth lumen and the outlet end of the second lumen comprises an enlarged portion, the enlarged portion having an internal diameter substantially equal to an external diameter of the other one of the inlet end of the fourth lumen and the outlet end of the second lumen.

3. The device of claim 1, wherein the third and fourth lumens of the nosepiece portion are formed from a flexible material.

4. The device of claim 3, wherein the third and fourth lumens of the nosepiece portion have a minimum radius of curvature of approximately one quarter inch along their respective lengths.

5. The device of claim 1, wherein the first and second lumens have a minimum radius of curvature of approximately one half inch along their respective lengths.

6. The device of claim 1, wherein the first and second lumens have approximately equal lengths.

7. The device of claim 1, wherein the constant internal diameter of the first lumen is equal to the constant internal diameter of the second lumen.

8. The device of claim 1, further comprising:
a connector adapted to be connected to the inlet ends of the first and second lumens without constricting the internal diameters of the first and second lumens.

9. A device for providing respiratory therapy to a patient comprising:
a first elongated lumen, the first lumen having an inlet end and an outlet end;
a second elongated lumen, the second lumen having an inlet end and an outlet end; and
a nosepiece portion configured to be connected to the outlet ends of the first and second lumens, the nosepiece portion having:

a third lumen having an inlet end adapted to be connected to the outlet end of the first lumen without constricting an internal diameter of the first lumen, the third lumen configured to receive a first flow of breathing gas from the first lumen and deliver the first flow of breathing gas to an outlet end of the third lumen;

a fourth lumen having an inlet end adapted to be connected to the outlet end of the second lumen without constricting an internal diameter of the second lumen, the fourth lumen configured to receive a second flow of breathing gas from the second lumen and deliver the second flow of breathing gas to an outlet end of the fourth lumen, the second flow of breathing gas maintained separate from the first flow of breathing gas within the nosepiece portion; and a source of heated and humidified breathing gas connected to the inlet ends of the first and second lumens, the source being configured to provide breathing gas at flow rates of about 40 liters per minute;

wherein the first lumen and the nosepiece portion define a constant diameter flow path for the first flow of breathing gas from the inlet end of the first lumen to the outlet end of the third lumen; and wherein the second lumen and the nosepiece portion define a constant diameter flow path for the second flow of breathing gas from the inlet end of the second lumen to the outlet end of the fourth lumen.

10. The device of claim 9, wherein
one of the inlet end of the third lumen and the outlet end of the first lumen comprises an enlarged portion, the enlarged portion having an internal diameter substantially equal to an external diameter of the other one of the inlet end of the third lumen and the outlet end of the first lumen, and
one of the inlet end of the fourth lumen and the outlet end of the second lumen comprises an enlarged portion, the enlarged portion having an internal diameter substantially equal to an external diameter of the other one of the inlet end of the fourth lumen and the outlet end of the second lumen.

11. The device of claim 10, wherein the third and fourth lumens of the nosepiece portion are formed from a flexible material.

12. The device of claim 11, wherein the third and fourth lumens of the nosepiece portion have a minimum radius of curvature of approximately one quarter inch along their respective lengths.

13. The device of claim 11, wherein the first and second lumens have a minimum radius of curvature of approximately one half inch along their respective lengths.

14. The device of claim 11, wherein the first and second lumens have approximately equal lengths.

15. The device of claim 14, wherein the internal diameter of the first lumen is about equal to the internal diameter of the second lumen.

16. The device of claim 15, further comprising:
a connector adapted to be connected to the inlet ends of the first and second lumens without constricting the internal diameters of the first and second lumens.

* * * * *